United States Patent [19]
Goralski

[11] 4,264,774
[45] Apr. 28, 1981

[54] 2-THIOPHENESULFONYL BROMIDES

[75] Inventor: Christian T. Goralski, Midland, Mich.

[73] Assignee: The Dow Chemical Company, Midland, Mich.

[21] Appl. No.: 744,216

[22] Filed: Nov. 22, 1976

[51] Int. Cl.³ .................... C07D 333/12; A61K 31/38
[52] U.S. Cl. ....................................... 549/66; 424/275
[58] Field of Search ........................ 260/332.5; 549/66

[56] References Cited
PUBLICATIONS

Van Quy "Chem. Abst." vol. 72 (1970) p. 21605c.
Siedel "Chem. Abst." vol. 56 p. 456f.

Primary Examiner—Alan Siegel

[57] ABSTRACT

2-Thiophenesulfonyl bromides having up to three additional substituents on the thiophene moiety selected from the group $C_{1-4}$ alkyl, chloro and bromo. The compounds have antimicrobial utility.

10 Claims, No Drawings

2-THIOPHENESULFONYL BROMIDES

SUMMARY OF THE INVENTION

This invention concerns 2-thiophenesulfonyl bromides represented by the formula

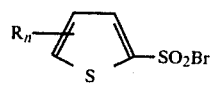

wherein $R_n$ represents from 1 to 3 members of the group H, $C_{1-4}$ alkyl, chloro and bromo. The compounds have antimicrobial activity.

The compounds are made by first preparing the corresponding chlorides by the method of C.A. 56 456f; German Pat. No. 1,088,509. The prior art 2-thiophenesulfonyl chlorides are converted into the bromides herein claimed by the method represented by the following schematic equation:

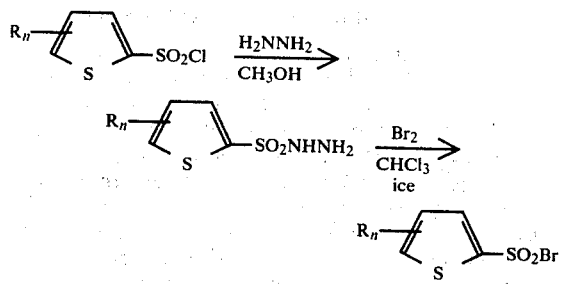

In the reaction, excess hydrazine in the presence of a solvent, advantageously a lower alkanol, is reacted with the 2-thiophenesulfonyl chloride to form a 2-thiophenesulfonyl hydrazine. In the reaction, the 2-thiophenesulfonyl chloride is gradually added to the hydrazine solution which is maintained at a low temperature, advantageously between about 5° and up to about 15° C. The reaction mixture is then allowed to warm to room temperature, the solvent is removed in vacuo and a mixture of a heavy oil and a fluffy solid results. This mixture is treated with water and the solid is dissolved and the oil separated therefrom. This mixture of oil and water, which contains the hydrazine hydrochloride from the first reaction, is then placed in a flask containing a bromine solvent, advantageously chloroform, crushed ice is added thereto and to the resulting slurry bromine is added at such a rate that the reaction temperature remains below about 10° C. After the bromine has been added and the bromine color has dissipated, the layers are separated, the chloroform layer is dried over an appropriate desiccant, advantageously anhydrous magnesium sulfate, and the chloroform removed in vacuo to leave a yellow oil which crystallizes on addition of hexane to give the 2-thiophenesulfonyl bromide.

The compounds of this invention have antimicrobial utility. In conventional in vitro agar Petri dish dilution tests, the following compounds and some corresponding art compounds gave 100% inhibition of the following organisms at the indicated concentrations in parts per million.

Compound

| $R_n$ | Sa | Ec | Ca | Tm | An | Bs | Aa | Cp | Pp | St | Ps 10 | Mp | Rn | Cl | Tr 42 |
|---|---|---|---|---|---|---|---|---|---|---|---|---|---|---|---|
| H | 500 | 100 | 100 | 100 | 100 | 100 | 100 | 100 | 100 | 100 | 100 | 100 | 100 | 100 | 100 |
| 5-Cl | 500 | 100 | 100 | 100 | 100 | 500 | 500 | 100 | 100 | 100 | 500 | 500 | 100 | 100 | 100 |
| 5-Br | 500 | 500 | 100 | 100 | 100 | 100 | 500 | 100 | 100 | 100 | 100 | 500 | 100 | 100 | 100 |
| 5-$CH_3$ | 100 | — | >100 | >100 | >100 | >100 | >100 | >100 | >100 | 50 | 50 | — | — | >100 | >100 |
| 5-$C_2H_5$ | 500 | 500 | 500 | 100 | 100 | 100 | 500 | 100 | 100 | 100 | 100 | — | 100 | 100 | 100 |
| 5-butyl | 500 | 500 | 500 | 100 | 100 | 100 | 500 | 100 | 100 | 100 | 500 | — | 100 | 100 | 100 |
| 3,5-$Br_2$ | 50 | — | 100 | 50 | — | 50 | 50 | 50 | 100 | 50 | 50 | — | — | 100 | 100 |
| 4,5-$Br_2$ | 50 | — | 100 | 100 | 100 | 50 | 100 | 100 | 100 | 50 | 50 | — | — | 100 | 100 |
| 3,4,5-$Br_3$ | 50 | — | 100 | 50 | 50 | 50 | >100 | 50 | 50 | 50 | 50 | — | — | 50 | 50 |

Compound

| $R_n$ | Sa | Ec | Ca | Tm | An | Bs | Aa | Cp | Pp | St | Ps 10 | Mp | Rn | Cl | Tr 42 |
|---|---|---|---|---|---|---|---|---|---|---|---|---|---|---|---|
| H | >500 | >500 | >500 | >500 | >500 | >500 | >500 | >500 | >500 | >500 | >500 | 500 | >500 | >500 | >500 |
| 5-$CH_3$ | " | " | " | " | " | " | " | " | " | " | " | — | " | " | " |
| 5-$C_2H_5$ | " | " | " | " | " | " | " | " | " | * | " | — | " | " | " |
| 5-butyl | * | " | " | 500 | " | * | " | * | " | >500 | " | — | " | " | " |
| 3,5-$Br_2$ | >100 | — | >100 | >100 | >100 | >100 | >100 | >100 | >100 | >100 | >100 | — | — | >100 | >100 |
| 4,5-$Br_2$ | " | — | " | 100 | " | " | " | " | 100 | " | " | — | — | " | " |

-continued

| | | | | MIC, ppm | | | | | | | | |
|---|---|---|---|---|---|---|---|---|---|---|---|---|
| 3,4,5-Br₃ | " | — | " | >100 | " | " | " | >100 | " | " | " | — | — | " | " |

The compounds under the double line and their data concern prior art compounds.
— = not tested
* = 50% inhibition at 500 ppm
Sa = S. aureus
Ec = E. coli
Ca = C. albicans
Tm = T. mentagrophytes
An = A. niger
Bs = B. subtilis
Aa = A. aerogenes
Cp = C. pelliculosa
Pp = P. pullulans
St = S. typhosa
Ps 10 = Pseudomonas Sp. Strain 10
Mp = M. phlei
Rn = R. nigricans
Cl = C. IPS
Tr 42 = T. Sp. Madison P-42

DESCRIPTION OF SOME PREFERRED EMBODIMENTS

The following additional description and examples further describe the invention and the manner and process of making and using it to enable the art skilled to make and use the same and set forth the best mode contemplated by the inventors of carrying out the invention.

EXAMPLE 1

2-Thiophenesulfonyl Bromide

In a 500 ml Erlenmeyer flask equipped with a magnetic stirrer and a thermometer were placed 200 ml of methanol and 6.80 g (0.20 mol) of 95% hydrazine. This solution wa cooled to 7° C. and 18.26 g (0.10 mol) of 2-thiophenesulfonyl chloride was added portion-wise in such a manner that the temperature did not exceed 15° C. After the addition was complete, the reaction mixture was allowed to warm to room temperature. The methanol was removed in vacuo leaving a mixture of a heavy oil and a fluffy solid. The mixture was treated with water, and the solid dissolved and oil separated. The mixture of oil and water (which contained the hydrazine hydrochloride from the first reaction) was placed in a flask containing 300 ml of chloroform and a magnetic stirrer. Crushed ice was added and to the resulting slurry 64.0 g of bromine was added at such a rate that the reaction temperature remained below 10° C. After the addition was complete and the bromine color had dissipated, the layers were separated. The chloroform layer was dried over anhydrous magnesium sulfate, and the chloroform removed in vacuo leaving a yellow oil which crystallized on addition of hexane. The solid was filtered and dried to give 15.33 g of the title compound as slightly yellow crystals, mp 49°–51° C.

Anal. Calcd for $C_4H_3BrO_2S_2$: C, 21.15; H, 1.33; Br, 35.19; S, 28.24. Found: C, 21.50; H, 1.30; Br, 34.90±0.2; S, 28.36.

EXAMPLE 2

5-Chloro-2-thiophenesulfonyl Bromide

In a 1-liter, three-neck flask equipped with a magnetic stirrer, a thermometer, an an addition funnel were placed 300 ml of methylene chloride, 10.63 g (0.05 mol) of 5-chloro-2-thiophenesulfonyl hydrazine, and some crushed ice. The slurry was allowed to cool to 2° C., and 16.0 g (0.10 mol) of bromine was added dropwise with stirring at such a rate that the temperature did not exceed 10° C. After the addition was complete, the methylene chloride layer was separated, dried and the methylene chloride removed in vacuo, leaving a yellow-orange oil. The oil was dissolved in hexane and the resulting solution cooled to give 6.56 g of the title compound as slightly yellow crystals, mp 35°–37°.
Anal. Calcd for $C_4H_2BrClO_2S_2$: C, 18.37; H, 0.77; Br, 30.55; Cl, 13.55; S, 24.52. Found: C, 18.40; H, 0.78; Br, 30.50; Cl, 13.10; S, 24.90.

EXAMPLE 3

5-Bromo-2-thiophenesulfonyl Bromide

To a slurry of 6.43 g (0.025 mol) of 5-bromo-2-thiophenesulfonyl hydrazine and some crushed ice in 100 ml of chloroform was added 8.0 g (0.05) of bromine dropwise with stirring. After the addition was complete and all of the bromine color had disappeared, the chloroform layer was separated and dried over anhydrous magnesium sulfate. The chloroform was removed in vacuo, leaving an orange oil. The oil was dissolved in ether/hexane and cooled to crystallize 3.67 g of the title compound as off-white crystals, mp 48°–50°.
Anal. Calcd for $C_4H_2Br_2O_2S_2$: C, 16.00; H, 0.78; Br, 52.00; S, 21.00. Found: C, 15.70; H, 0.66; Br, 52.23; S, 20.96.

EXAMPLE 4

Pursuant to the procedures of Examples 1–3, the following sulfonyl bromides were prepared:

| Compound | Melting Point, °C. | Elemental Analyses, % |
|---|---|---|
| 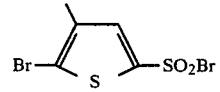 | 83–84 | Anal. Calc. for $C_4HBr_3O_2S_2$: C, 12.48; H, 0.26; Br, 62.28; S, 16.66. Found: C, 12.29; H, 0.32; Br, 62.3; S, 16.90. |

| Compound | Melting Point, °C | Elemental Analyses, % |
|---|---|---|
| [Br, Br, Br, SO₂Br on thiophene] | 69 | Anal. Calc. for C₄HBr₃O₂S₂: C, 12.48; H, 0.26; Br, 62.28; S, 16.66. Found; C, 13.20; H, 0.39; Br, 62.50 ± 0.5; S, 16.90. |
| [Br, Br, Br, SO₂Br on thiophene] | 82–83 | Anal. Calc. for C₄Br₄O₂S₂: C, 10.36; S, 13.83. Found: C, 10.30; S, 14.50. |
| CH₃-thiophene-SO₂Br | yellow oil* | |
| CH₃CH₂-thiophene-SO₂Br | yellow oil* | |
| CH₃CH₂CH₂CH₂-thiophene-SO₂Br | yellow oil* | |

*These products were not distilled to avoid decomposition. They were identified by their nmr spectra which were in agreement with the structures assigned.

What is claimed is:

1. A compound represented by the formula

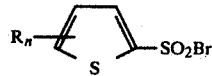

wherein R represents H, $C_{1-4}$ alkyl, chloro or bromo and n represents an integer from 1 to 3.

2. The compound of claim 1 wherein $R_n$ represents H.

3. The compound of claim 1 wherein $R_n$ represents 5-methyl.

4. The compound of claim 1 wherein $R_n$ represents 5-ethyl.

5. The compound of claim 1 wherein $R_n$ is 5-butyl.

6. The compound of claim 1 wherein $R_n$ is 5-chloro.

7. The compound of claim 1 wherein $R_n$ is 5-bromo.

8. The compound of claim 1 wherein $R_n$ is 3,5-dibromo.

9. The compound of claim 1 wherein $R_n$ is 4,5-dibromo.

10. The compound of claim 1 wherein $R_n$ is 3,4,5-tribromo.

* * * * *